(12) United States Patent
Koop et al.

(10) Patent No.: US 6,273,885 B1
(45) Date of Patent: Aug. 14, 2001

(54) HANDHELD PHOTOEPILATION DEVICE AND METHOD

(75) Inventors: Dale E. Koop, Woodside; Mark D. Selker, Palo Alto; Timothy J. Johnston, Mountain View, all of CA (US)

(73) Assignee: CoolTouch Corporation, Roseville, CA (US)

( * ) Notice: Subject to any disclaimer, the term of this patent is extended or adjusted under 35 U.S.C. 154(b) by 0 days.

(21) Appl. No.: 09/135,330

(22) Filed: Aug. 16, 1998

Related U.S. Application Data

(60) Provisional application No. 60/055,925, filed on Aug. 16, 1997, now abandoned.

(51) Int. Cl.[7] ................................................ A61B 18/18
(52) U.S. Cl. ................................................ 606/9; 607/89
(58) Field of Search .................. 606/20, 9, 10, 606/11, 12, 14, 15, 16, 17, 19; 607/88, 89

(56) References Cited

U.S. PATENT DOCUMENTS

| | | |
|---|---|---|
| Re. 36,634 * | 3/2000 | Ghaffari ................................ 606/9 |
| 3,821,510 | 6/1974 | Muncheryan . |
| 4,388,924 | 6/1983 | Weissman et al. . |
| 4,733,660 | 3/1988 | Itzkan . |
| 4,976,709 | 12/1990 | Sand . |
| 5,020,995 | 6/1991 | Levy . |
| 5,057,104 | 10/1991 | Chess . |
| 5,098,428 | 3/1992 | Sandlin et al. . |
| 5,137,530 | 8/1992 | Sand . |
| 5,217,455 | 6/1993 | Tan . |
| 5,259,380 | 11/1993 | Mendes et al. . |
| 5,282,797 * | 2/1994 | Chess ................................... 606/9 |
| 5,304,169 | 4/1994 | Sand . |
| 5,344,418 | 9/1994 | Ghaffari . |
| 5,358,503 * | 10/1994 | Bertwell et al. ..................... 606/9 |
| 5,374,265 | 12/1994 | Sand . |
| 5,484,432 | 1/1996 | Sand . |
| 5,486,172 * | 1/1996 | Chess ................................. 606/20 |
| 5,595,568 * | 1/1997 | Anderson et al. .................... 606/9 |
| 5,630,811 * | 5/1997 | Miller ................................... 606/9 |
| 5,707,403 * | 1/1998 | Grove et al. ....................... 607/89 |
| 5,707,684 * | 1/1998 | Hayes ............................... 427/162 |

(List continued on next page.)

OTHER PUBLICATIONS

Anvari et al., Selective Cooling of Biological Tissues: Application for Thermally Mediated Therapeutic Procedures. *Phys. Med. Biol.* 40 (1995) 241–252.

(List continued on next page.)

*Primary Examiner*—Roy Gibson
(74) *Attorney, Agent, or Firm*—Ray K. Shahani, Esq.

(57) ABSTRACT

A laser tissue treatment device capable of being handheld, the device comprising a semiconductor diode or diode array laser which emits energy and a device for surface cooling of tissue such that the energy is directed through said cooling device in contact with tissue. The diode laser operates at wavelengths between about 630 nm and 980 nm, and delivers a predetermined amount of energy in a predetermined period of time and having a predetermined spot size. The device utilizes one or more microlenses or microlens arrays to collimate the diode laser energy. Optionally, the device utilizes a deflecting optic for deflecting the diode laser energy through the cooling device which is in contact with tissue in which the deflecting optic is visually transparent such that the operator can see the tissue treatment area. A cooling device such as a sapphire plate or other active or passive cooling means is used to cool the tissue. A method for treatment of tissue, including hair removal, with a handheld device comprises generating laser energy from a semiconductor diode laser, directing the energy through a cooling device in contact with tissue, and treating tissue with the laser energy.

16 Claims, 2 Drawing Sheets

U.S. PATENT DOCUMENTS

| | | | | |
|---|---|---|---|---|
| 5,743,901 | * | 4/1998 | Grove et al. | 606/9 |
| 5,800,479 | * | 9/1998 | Thiberg | 607/88 |
| 5,802,092 | * | 9/1998 | Endriz | 372/50 |
| 5,810,801 | * | 9/1998 | Anderson et al. | 606/9 |
| 5,814,040 | | 9/1998 | Nelson et al. . | |
| 5,820,625 | * | 10/1998 | Izawa et al. | 606/9 |
| 5,820,626 | | 10/1998 | Baumgardner . | |
| 5,830,208 | * | 11/1998 | Muller | 606/9 |
| 5,853,407 | * | 12/1998 | Miller | 606/9 |
| 5,868,732 | * | 2/1999 | Waldman et al. | 606/9 |
| 5,879,346 | * | 3/1999 | Waldman et al. | 606/9 |
| 5,879,376 | * | 3/1999 | Miller | 607/8 |

OTHER PUBLICATIONS

Anvari et al., Spatially Selective Photocoagulation of Biological Tissues: A Feasibility Study Utilizing Cryogen Spray Cooling. *App. Optics*, in press as of 1–8–96.

Duque et al., Abstract 187: "Long Pulsed Ruby laser for Hair Removal; Comparison between Different Spot Sizes, Temperatures and Interval Between First and Second Treatment", *Lasers in Surgery and Medicine*, Proceedings of the American Society for Laser Medicine Surgery 18$^{th}$ Annual Meeting in San Diego, California, Apr. 5–7, 1998. (Applicant is aware of an audio tape recording of the oral presentation.)

Jenoptik Laserdiode GmbH product information: Actively cooled diode laser stack specification sheet, part No. 20282126 schematic, etc., 4 pages.

Kincade, K., New Procedures Push Tissue Studies Beneath the Surface. *Laser Focus World*, 57–63 (Aug. 1995).

Omega Micro Infrared Temperature Transducer OS40 Series. Omega Complete Temperature Measurement Handbook and Encyclopedia (a registered trademark), vol. 28, pages cover, J–45 and J–46 (1992).

Reliant Technologies, Inc., Accu–Scan. Product News, Jan. 25, 1995, 2 pages.

Handpiece Extender brochure, Spectrum Medical Technologies, Inc., RD 1100, RD 1200, 2 pages.

* cited by examiner

HANDHELD PHOTOEPILATION DEVICE AND METHOD

RELATED INVENTIONS

This Application claims benefits under 35 U.S.C. § 119(e) of U.S. Provisional Application Ser. No. 60/055,925 filed Aug. 16, 1997 now abandoned entitled Handheld Photoepilation Device and Method.

FIELD OF THE INVENTION

The invention described is a device and method for photoepilation using a handheld high power semiconductor diode laser based system. The optical energy delivered by the semiconductor laser is absorbed preferentially by melanin in the skin and converted to thermal energy in and around the hair follicles, thus reducing or eliminating their ability to produce hair.

BACKGROUND OF THE INVENTION

Laser based photoepilation has been the object of study since the advent of the laser. It has been know for several years that optical pulses of the appropriate wavelength, pulse duration, and energy density impinging upon human skin will result in significant and enduring hair loss. The accepted theory for this phenomenon is that the penetration of the laser into the skin and its subsequent scattering results in heating of the hair shafts and follicles through selective absorption by melanin. The absorption of the radiation leads to heating of the follicle and subsequent thermal necrosis.

It has been found that for effective photoepilation to occur the energy must be penetrate approximately 3 mm into the tissue. Prevailing thought indicates that this means the absorption should occur in the melanin and not the oxyhemoglobin, thereby heating the regions around the hair follicle instead of heating the blood and blood vessels. Energy absorption in the melanin leads to elimination of the hair and the reduction or elimination of the ability of follicle to produce hair. Based on the absorption spectrum of melanin and oxyhemoglobin the wavelengths in the neighborhood of 700 nm have been thought to be efficacious. Therefore the Ruby laser at 694 nm, the Alexandrite laser around 760 nm, and flashlamps with emission spectrum centered near 700 nm have been used for this application. The aforementioned lasers are very inefficient, requiring high voltages, large supplies of cooling water. In addition, delivery of the energy to the skin surface is problematic due to the energy required for photoepilation. The pulse energies often exceed damage thresholds of delivery systems or are difficult channel to from the laser to the skin. The flashlamps themselves are inefficient, emit in all directions making efficient energy delivery difficult, and the flashlamps can be cumbersome to use in a handheld device. The convenient and controlled delivery of the optical energy of the appropriate wavelength, fluence and pulse duration to the skin surface for photoepilation in an efficient device has been difficult.

ADVANTAGES AND SUMMARY OF THE INVENTION

The epilation process is dependent on 3 basic parameters: wavelength, total mount of energy deposited or delivered, and pulsewidth. High power semiconductor diodes are the only devices that allow the flexibility change all three parameters in the optical pulses as the situation requires. Current lasers (e.g. Ruby and Alexandrite ) are limited in their ability to deliver the energy in the optimal time period. In addition, their small size allows them to be placed in a handheld unit allowing for ease of patient treatment. Finally, their lifetimes are significantly longer than flashlamp based laser systems currently in use.

The prior art displaced by a handheld semiconductor diode device is the flashlamp pumped Ruby laser, the flashlamp pumped Alexandrite laser and handheld flashlamp systems. All of the aforementioned systems suffer from the fact that they require high voltage in order to drive the flashlamps which have a lifetime considerably less than that of the diode laser. In addition, the diode laser arrays are much smaller than flashlamps, making a handheld device easier to use and position on the area to be treated.

Thus, it is an advantage of the present invention to provide a handheld, semiconductor diode laser or diode array device, optionally having an active or passive heat sink or thermal conduction plate for maintaining the surface temperature of the skin from overheating, for photoepilation and other dermatological applications.

It is a further advantage of the present invention to provide a semiconductor diode laser or diode array having a microlens or microlenses for shaping, confluencing, or otherwise optically modifying. the laser produced by the diode laser, diodes or diode array.

It another advantage of the present invention to provide such a handheld photoepilation system which requires lower voltage than conventional flashlamp pumped ruby or alexandrite or other type lasers.

The described invention provides an improved laser system for performing treatment of skin, including but not limited to photoepilation. One embodiment of the improved laser system is a handheld device comprising a semiconductor diode laser and chilled plate that transmits the laser energy to the skin. The transparent chilled plate is used in order to keep the temperature of the epidermis low enough to avoid significant thermally induced damage.

The semiconductor diode laser comprises a diode array or a single element device produces a fluence level of approximately 20–40J/cm$^2$. The semiconductor laser would be typically operated in a pulsed mode with pulsewidths between approximately 1 millisecond and where the wavelength of the semiconductor diode laser is between approximately 630 nm and 980 nm.

Additionally, the semiconductor diode laser energy can be collimated using a micro-lens array or other focusing elements in order to obtain the appropriate fluence. In another embodiment, the collimated semiconductor diode laser energy is reflected off of a polarizer or dichroic plate so that the user can observe the region of skin while the diode laser energy is impinging upon the skin.

Another embodiment of the handheld device is a system where the energy is transmitted to the handpiece using one or more optical fibers. The handpiece includes the optical fiber(s) and, optionally, a set of lenses used to collimate the energy transmitted through a chilled transparent plate.

The device described here is a handheld, diode laser based system for delivering optical pulses. An optimal wavelength for epilation is approximately 700 nm since the oxyhemoglobin absorption is a minimum here while absorption by the melanin is still significant. Currently standard high power diodes are available from roughly 780 nm to 870 nm, and the present device uses high power diode arrays, optionally micro-lensed high power diode arrays, which produce wavelengths in the range from 780 nm to 830 nm.

The energy would be delivered in a spot size of approximately about 1 cm$^2$. The energy would be delivered in less than 1 second, and typically in less than 50 milliseconds, with a peak power of approximately 1 Kw. One embodiment of the device would utilize a transparent plate that is cooled in conjunction with the high power diodes. The purpose of the chilled transparent plate is to allow the diode energy through while simultaneously reducing the temperature of the epidermis thereby reducing heat induced damage to the epidermis.

Numerous other advantages and features of the present invention will become readily apparent from the following detailed description of the invention and the embodiments thereof, from the claims and from the accompanying drawings.

DETAILED DESCRIPTION OF THE PREFERRED EMBODIMENT

Figure 1:
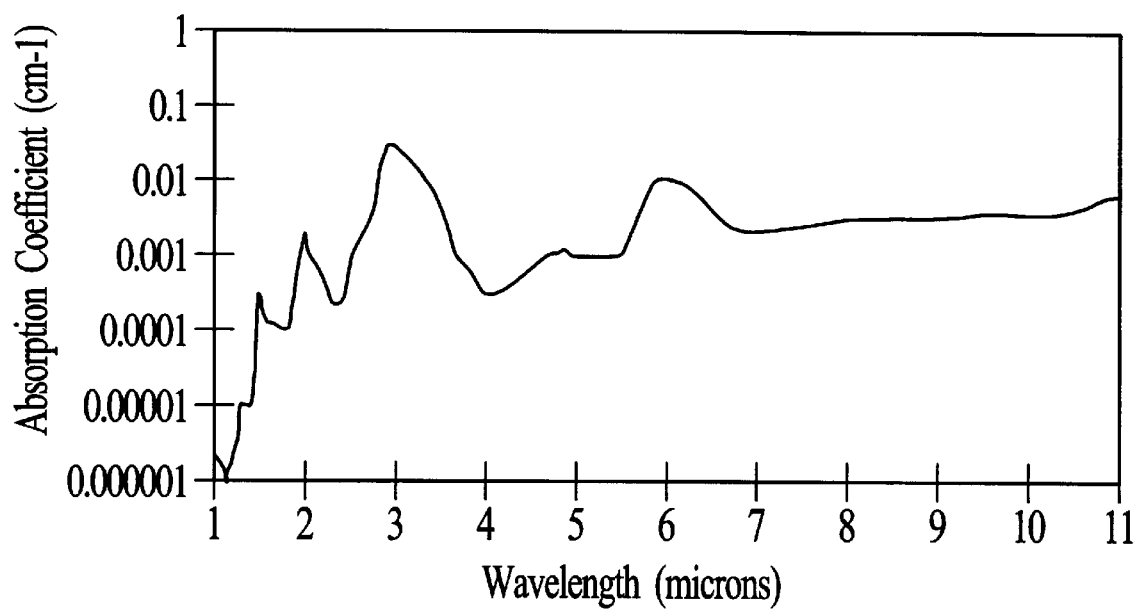
FIG. 1 is a graph of the absorption coefficient of melanin and oxyhemoglobin as a function of wavelength of electromagnetic energy.

It will be understood that while numerous preferred embodiments of the present invention are presented herein, numerous of the individual elements and functional aspects of the embodiments are similar. Therefore, it will be understood that structural elements of the numerous apparatus disclosed herein having similar or identical function may have like reference numerals associated therewith.

FIG. 1 is a graph of the absorption coefficient in $cm^{-1}$ versus wavelength for the oxyhemoglobin and the melanin in typical skin tissue. It can be seen that there exists a plurality of wavelengths around 700 nm where the melanin absorption coefficient is finite and larger than the oxyhemoglobin absorption coefficient, a minimum at around 700 nm is observed.

Figure 2:
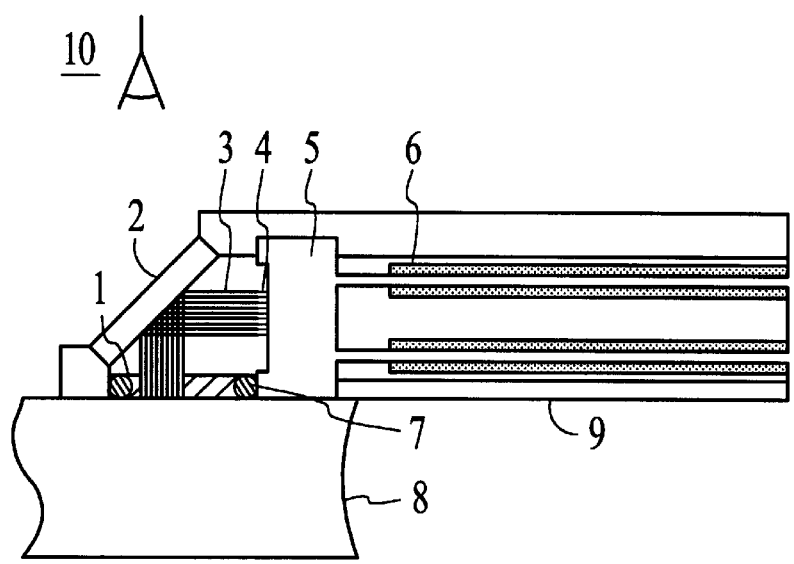
FIG. 2 is a drawing of a handheld device using a micro lens collimated beam from a semiconductor diode laser, where the user can see the skin surface as the energy is delivered through a chilled transparent plate.

FIG. 2 shows a system comprising handheld housing 9, contain semiconductor diode laser 5. The semiconductor diode energy 3 emitted from semiconductor diode laser 5 is collimated using such optical elements including but not limited to one or more or an array of micro-lenses 4. Semiconductor diode laser 5 is cooled using water flowing to impingement cooler 6, or can use a finned, high heat capacity material for passive cooling.

Diode energy 3 can be directed to skin 8 in such a way that the device user can observe the tissue being treated from viewing point 10. Diode energy 3 is reflected off of an optical element 2 such as a polarizer or a dichroic coating, while the ambient light illuminating tissue 8, is reflected and viewed at 10. Energy 3 is transmitted through a transparent chilled plate 1 which can be made of substances including but not limited to sapphire. The temperature of transparent plate 1 is reduced by the presence of cooling water circulating in thermally conductive tubing 7 around the plate or by channels made directly in the plate. Another method of chilling the plate is though the use of thermoelectric coolers.

The semiconductor array can be made of cw (continuous wave) or quasi-cw diode bars. Depending on the peak power of the diode bars, a set of micro lenses or a micro lens array or other focusing device may be required in order to reach the desired fluence level of approximately 20–40J/$cm^2$. The optimal wavelength is approximately 700 nm, which has a minimal absorption wavelength for oxyhemoglobin, but where melanin has significant absorption. Currently, high power semiconductor diode arrays are made using AlGaAs, and InGaAs and are available continuously from approximately 780 nm to 870 mn.

FIG. 1 uses an optical element 2 such as a polarizing plate or dichroic beam splitter at approximately 45 degrees. This allows the diode array energy to be directed to the treatment area while allowing the user to see the treatment area. The micro-lenses or other collection optics are required in order keep the energy density at an appropriate level while projecting it off of the polarizer or dichroic beamsplitter to the treatment area.

Figure 3:
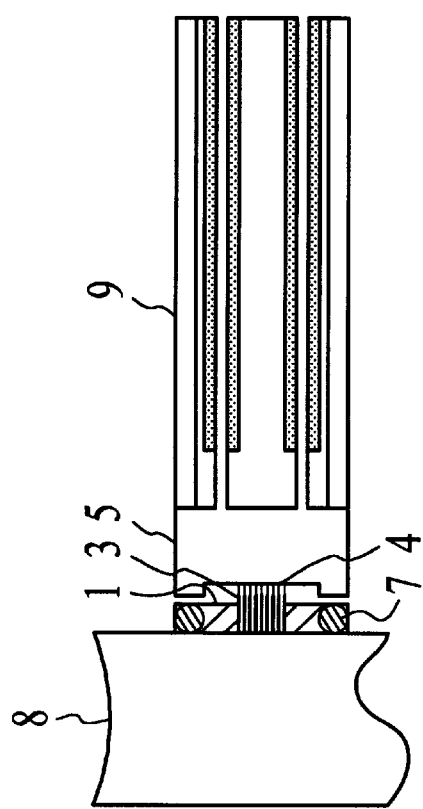
FIG. 3 is a drawing of a handheld device using one or more semiconductor diode laser arrays collimated and transmitted directly through a chilled transparent plate.

FIG. 3 is a preferred embodiment of a system comprising handheld housing 9 containing semiconductor diode laser 5 which is cooled using chilled water flowing to impingement cooler 6, or can use a finned high heat capacity material as a heatsink for passive cooling. Semiconductor diode energy 3 can be collimated using optical elements such as microlens array 4, or can be allowed to diverge freely and impinge upon tissue to be treated 8.

Semiconductor energy 3 is transmitted through a transparent chilled plate 1 which can be made of substances including but not limited to sapphire. The temperature of transparent plate 1 is reduced by the presence of cooling water circulating in thermally conductive tubing 7 around the plate or by channels made directly in the plate. The chill plate can also be chilled through use of thermoelectric coolers.

The array(s) can be used in a variety of handheld embodiments depending on the application and type of array used. In a preferred embodiment, a handheld device utilizes a high power semiconductor array, with the optimal distance to the epidermis set by the thickness of the cover plate which is transparent to the diode energy. The transparent cover plate can be chilled to reduce thermal damage to the epidermis.

In preferred embodiments, the diode array is collimated using a micro-lens array. The diodes can be collimated using various other optical concentration methods. The micro lenses or optical collection devices serve to increase the fluence in order reach the goal of approximately 20–40J/cm2.

Figure 4:
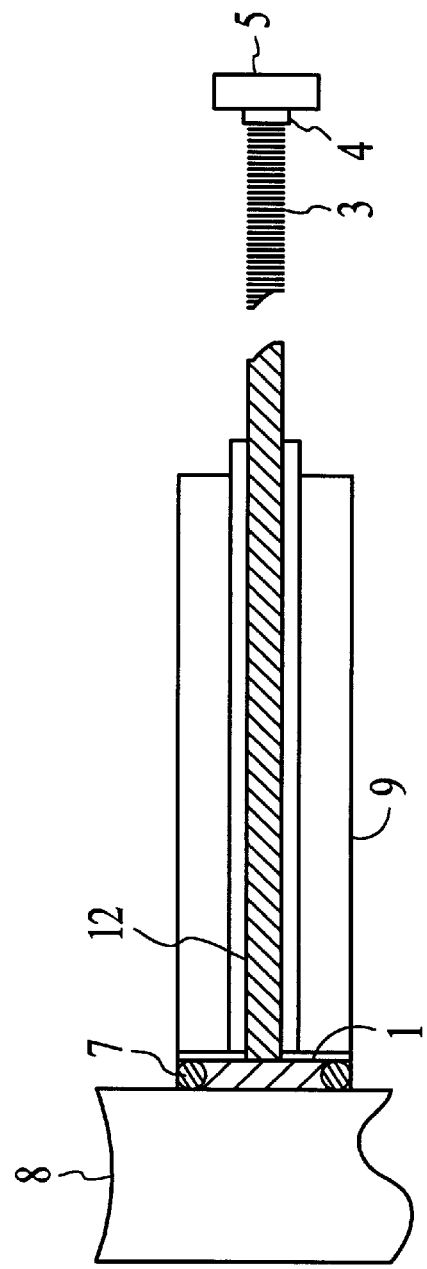
FIG. 4 is a drawing of an embodiment of the device where the energy is transmitted to a handpiece using optical fibers.

FIG. 4 depicts an embodiment of the invention comprising high power semiconductor laser 5 from which the optical energy 3 emitted is coupled to optical fibers 12 using microlenses 4; the energy 3 can also be directly coupled in optical fibers 12. Optical fibers 12 pass through to housing 9. The remitted optical energy from transport fiber 12 passes through chilled plate 1 which is in contact with tissue 8 to be treated. The temperature of transparent plate 1 is reduced by the presence of cooling water circulating in thermally conductive tubing 7 around the plate or by channels made directly in the plate. The chill plate can also be chilled through use of thermoelectric coolers.

Preferred embodiments of the energy delivery system operate at about $\geq 15$ Joules (which is equivalent to about $\geq 400$ watts continuous wave). An optimum pulse duration is $\leq 50$ milliseconds, and operates at between about 630 nm and about 980 nm, produces a spot size of about 1 $cm^2$, has a small chiller for cooling plate and diodes, weighs 1.5 pounds and is the size of a flashlight. It operates at between about 15° Celsius and about 35° Celsius on 120 volt, single phase power.

Stacked arrays and microlensed arrays are available from companies such as Jenoptik Laserdiode GmbH, Prussingstr, Germany. A typical array might be rated at 330 watts and include drivers to operate them safely. Stacks such as QCW stacks with small pitch/low duty cycle can be used, such as multi-bar stacks with pitch between about 100 microns to about 2.0 millimeters. High power cw stacks exist which are water cooled through microchannel heatsinks. The expected lifetime of these devices is >5000 hours (MTBF). It may be necessary to drive the diodes past their specified power rating by a factor of 2 or more. Specifically, optimum performance will be achieved with >400 watts and preferably >600 watts delivered in under or about 50 milliseconds, to reach the desired energy fluence level. Obviously, the lifetime of the product can be expected to be reduced to less than about 2000 hours, with the system designed to employ the diode array as a consumable and easily replaceable item.

Unless defined otherwise, all technical and scientific terms used herein have the same meaning as commonly understood by one of ordinary skill in the art to which this invention belongs. Although any methods and materials similar or equivalent to those described can be used in the practice or testing of the present invention, the preferred methods and materials are now described. All publications and patent documents referenced in this application are incorporated herein by reference.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true purview, spirit and scope of the invention.

We claim:

1. A laser tissue treatment device capable of being handheld, the device comprising:
   an array of semiconductor diode lasers which emits energy;
   micro-lens array means for collimating the laser energy, and;
   a device for surface cooling of tissue, the device comprising a visually transparent deflecting optic for deflecting the diode laser energy through the cooling device in contact with tissue.

2. The device of claim 1, wherein the semiconductor diode laser power is greater than 100 watts.

3. The device of claim 1 wherein the diode laser operates in pulsed mode.

4. The device of claim 1 wherein the diode laser operates in pulsed mode with pulse durations between 1 millisecond and 1 second.

5. The device of claim 1 wherein the diode laser wavelength is between 630 nm and 980 nm.

6. The device of claim 1 wherein the diode laser wavelength is between 690 nm and 800 nm.

7. The device of claim 1 wherein the deflecting optic is thermally isolated from the cooling device, which is in contact with tissue, so as to avoid condensation on the deflecting optic.

8. The device of claim 7 wherein the cooling device is sealed such that condensation may occur only on the surface in contact with tissue.

9. The device of claim 1 wherein the cooling device is a sapphire plate cooled by a coolant.

10. The device of claim 9 wherein the coolant is circulating water.

11. A method for treatment of tissue with a handheld device, the device comprising a visually transparent deflecting optic for deflecting energy to the tissue, the method comprising:
    generating laser energy from an array of semiconductor diode lasers;
    collimating the laser energy with a micro-lens array;
    directing the energy through the cooling device to the tissue to be treated; and
    treating the tissue with the laser energy.

12. The method of claim 11 further comprising the step of visualization of the tissue to be treated.

13. The method of claim 11 further comprising the step of visualization of the tissue during treatment.

14. A method for hair removal using a handheld semiconductor diode laser device, the device comprising a visually transparent deflecting optic for deflecting energy to the tissue, the method comprising:
    generating laser energy from an array of semiconductor diode lasers;
    collimating the laser energy with a micro-lens array;
    directing the energy through a cooling device in contact with tissue; and
    treating tissue with the laser energy so as to cause enduring removal of unwanted hair.

15. The method of claim 11 further including the step of focusing the laser energy using focusing lens prior to directing the laser energy through the cooling device in contact with tissue.

16. A laser based tissue treatment device in which the energy from an array of semiconductor diode lasers is collimated utilizing a micro-lens array and coupled into and delivered via optical fibers to a handpiece, the handpiece comprising a visually transparent optical deflector for optically deflecting the energy to tissue through a cooling device.

* * * * *